(12) United States Patent
Hayakawa

(10) Patent No.: US 11,147,433 B2
(45) Date of Patent: Oct. 19, 2021

(54) DISTAL END COVER FOR ENDOSCOPE

(71) Applicant: OLYMPUS CORPORATION, Tokyo (JP)

(72) Inventor: Fumitoshi Hayakawa, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 357 days.

(21) Appl. No.: 16/364,283

(22) Filed: Mar. 26, 2019

(65) Prior Publication Data

US 2019/0216299 A1 Jul. 18, 2019

Related U.S. Application Data

(63) Continuation of application No. PCT/JP2017/043306, filed on Dec. 1, 2017.

(30) Foreign Application Priority Data

Dec. 2, 2016 (JP) .............................. JP2016-234851

(51) Int. Cl.
*A61B 1/00* (2006.01)
*A61B 1/018* (2006.01)
(Continued)

(52) U.S. Cl.
CPC ........ *A61B 1/00135* (2013.01); *A61B 1/0014* (2013.01); *A61B 1/00098* (2013.01);
(Continued)

(58) Field of Classification Search
None
See application file for complete search history.

(56) References Cited

U.S. PATENT DOCUMENTS 5,147,305 A * 9/1992 Nakamura ......... A61B 1/00062
604/110
5,662,588 A * 9/1997 Iida .................... A61B 1/00091
600/121
(Continued)

FOREIGN PATENT DOCUMENTS

EP 1849397 A1 10/2007
JP H09-075295 A 3/1997
(Continued)

OTHER PUBLICATIONS

International Search Report dated Jan. 16, 2018 issued in PCT/JP2017/043306.

*Primary Examiner* — Timothy J Neal
(74) *Attorney, Agent, or Firm* — Scully, Scott, Murphy & Presser, P.C.

(57) ABSTRACT

A distal end cover for endoscope according to an aspect of the present invention that is configured to be mounted on a distal end member provided with a raising stand of an insertion portion of the endoscope to cover a part of the distal end member, and has an opening portion through which a space accommodating the raising stand is exposed to an outside, is provided with a break inducing portion having a notch portion formed at a periphery portion on a distal end side of the opening portion, and a thin wall portion that is connected to the notch portion at a distal end of the thin wall portion, and extends in a proximal end direction, a rotation stopping portion that suppresses rotation of the distal end cover relative to the distal end member and a finger hooking portion.

5 Claims, 8 Drawing Sheets

(51) Int. Cl.
*G02B 23/24* (2006.01)
*A61B 90/00* (2016.01)

(52) U.S. Cl.
CPC .......... *A61B 1/00101* (2013.01); *A61B 1/018* (2013.01); *G02B 23/24* (2013.01); *A61B 1/00091* (2013.01); *A61B 2090/3966* (2016.02)

(56) References Cited

U.S. PATENT DOCUMENTS

| | | | | |
|---|---|---|---|---|
| 5,674,181 | A * | 10/1997 | Iida | A61B 1/0008 600/127 |
| 5,730,701 | A * | 3/1998 | Furukawa | A61B 1/0008 600/121 |
| 5,860,913 | A * | 1/1999 | Yamaya | A61B 1/00091 600/127 |
| 5,865,726 | A * | 2/1999 | Katsurada | A61B 1/12 600/127 |
| 5,868,663 | A * | 2/1999 | Katsurada | A61B 1/018 600/107 |
| 2004/0082836 | A1 * | 4/2004 | Hino | A61B 1/0008 600/170 |
| 2007/0246506 | A1 | 10/2007 | Hamazaki et al. | |
| 2008/0103357 | A1 * | 5/2008 | Zeiner | A61B 1/0014 600/104 |
| 2017/0238789 | A1 * | 8/2017 | Iizuka | A61B 1/00089 |
| 2018/0185045 | A1 * | 7/2018 | Ohki | A61B 1/00114 |

FOREIGN PATENT DOCUMENTS

| | | | |
|---|---|---|---|
| JP | 2003-102668 | A | 4/2003 |
| JP | 2007-289434 | A | 11/2007 |
| JP | 4855824 | B2 | 1/2012 |

\* cited by examiner

DISTAL END COVER FOR ENDOSCOPE

CROSS REFERENCE TO RELATED APPLICATION

This application is a continuation application of PCT/JP2017/043306 filed on Dec. 1, 2017 and claims benefit of Japanese Application No. 2016-234851 filed in Japan on Dec. 2, 2016, the entire contents of which are incorporated herein by this reference.

BACKGROUND OF THE INVENTION

1. Field of the Invention

The present invention relates to a distal end cover for endoscope which is configured to be mounted on a distal end member including a raising stand and configuring a distal end portion of an insertion portion of the endoscope.

2. Description of the Related Art

A side-viewing type endoscope (hereinafter referred to as an endoscope) in which an illumination lens and an objective lens are arranged on a side surface of a distal end side of an insertion portion, a so-called endoscope for duodenum is known as one endoscope for medical use. The endoscope is provided with a treatment instrument channel and a raising device.

A treatment instrument such as an imaging tube, a basket catheter, or a balloon catheter is inserted in the treatment instrument channel. The treatment instrument having passed through the treatment instrument channel is led out to the outside from a distal end opening provided in the distal end member, and the leading direction is switched to a desired direction by the raising device.

Generally, the raising device mainly includes a raising stand which is rotatably arranged on the distal end member, a raising stand operating lever provided to an operation portion, and a raising stand operating wire which moves in connection with the operation of the raising stand operating lever to swing the raising stand.

The distal end member is covered with a distal end cover for an electrically insulating endoscope. The distal end cover is fixed by an adhesive or the like in order to prevent the distal end cover from falling off from the distal end member.

The endoscope is cleaned and disinfected after use. It is known that when the insertion portion of the endoscope is cleaned, it is possible to expose a distal end port of the treatment instrument channel by removing the distal end cover from the distal end portion and easily perform cleaning.

For example, the specification of Japanese Patent No. 4855824 discloses a distal end cover that can be removed from a distal end member by tearing and breaking the distal end cover without damaging a flexible member configuring the insertion portion, and can be prevented from falling out during use.

The distal end cover for the endoscope is provided with a thin wall portion and a concaved groove serving as a plastically deformable portion for sequentially releasing a locking state based on a first locking portion, a second locking portion, and a third locking portion by plastically deforming the plastically deformable portion with a finger hooking portion as a starting point.

The thin wall portion is provided at a side surface portion between the finger hooking portion and the opening portion of the distal end cover for the endoscope. The concaved groove is formed on an inner peripheral surface over the entire periphery from a proximal end portion of the thin wall portion or the vicinity of the proximal end portion to a side surface portion, a front surface portion and a side surface portion on the opposite side of the distal end cover for the endoscope.

SUMMARY OF THE INVENTION

In order to attain the above object, a distal end cover for endoscope according to an aspect of the present invention that is configured to be mounted on a distal end member provided with a raising stand of an insertion portion of the endoscope to cover a part of the distal end member, and has an opening portion through which a space accommodating the raising stand is exposed to an outside, includes: a break inducing portion having a notch portion formed at a periphery portion on a distal end side of the opening portion, and a thin wall portion that is connected to the notch portion at a distal end of the thin wall portion, and extends in a proximal end direction; a rotation stopping portion that abuts against a wall surface portion rising up from an area of a surface along an insertion portion longitudinal axis out of an outer peripheral surface of the distal end member, thereby suppressing rotation of the distal end cover relative to the distal end member; and a finger hooking portion that protrudes outward from one side of an area along the insertion portion longitudinal axis out of the periphery portion of the opening portion relative to another side of the area, and arranged on an opposite side to the rotation stopping portion with respect to the opening portion and the break inducing portion when the finger hooking portion is viewed in a direction along the insertion portion longitudinal axis.

DETAILED DESCRIPTION OF THE PREFERRED EMBODIMENT(S)

A preferred embodiment of the present invention will be described hereinafter with reference to the drawings. Note that the scales of components are respectively made different in the figures used in the following description in order to make the components recognizable in size in the figures, and the present invention is not limited to the numbers of the components, the shapes of the components, the ratio of the sizes of the components, and the relative positional relationship of the components shown in these figures.

Figure 1:
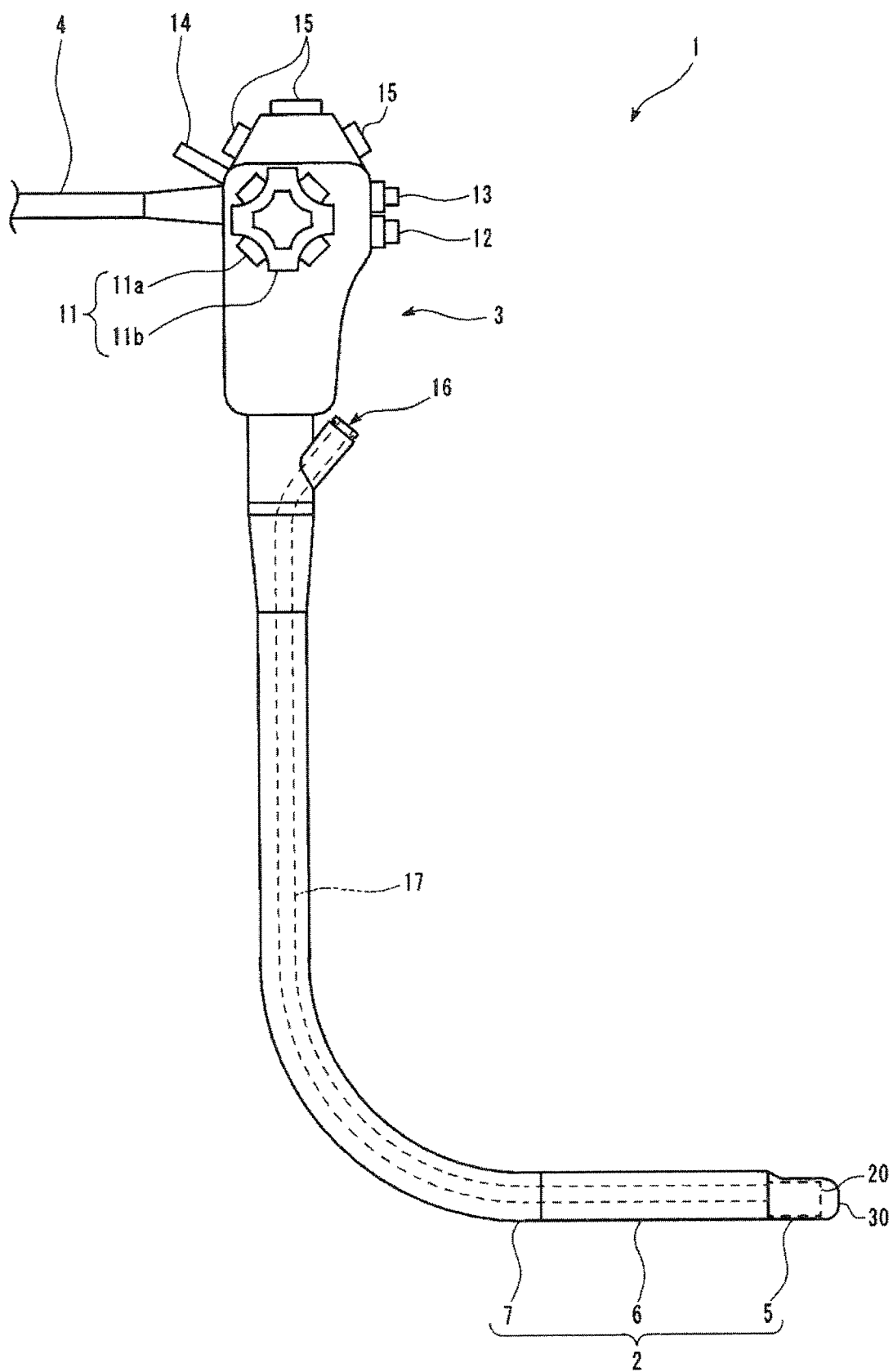
FIG. 1 is a diagram showing a schematic configuration of a side-viewing type endoscope.

A distal end cover 30 of the present embodiment is a distal end cover for a side-viewing type endoscope, which is configured to be mounted on a side-viewing type endoscope 1. FIG. 1 is a diagram showing a schematic configuration of the side-viewing type endoscope 1 having the distal end cover 30.

The endoscope 1 includes an insertion portion 2 to be inserted into a subject, an operation portion 3 provided on a proximal end side of the insertion portion 2, and a universal cord 4 extending from the operation portion 3.

The operation portion 3 is provided with a bending operation device 11, an air/water feeding button 12, a suction button 13, a raising stand operating lever 14, and various operation switches 15.

The operation switches 15 include a freeze switch configured to generate a freeze signal, a release switch configured to generate a release signal when photographing is performed, an observation mode changeover switch configured to instruct switching of an observation mode, and the like.

The operation portion 3 is provided with a treatment instrument insertion port 16 through which a treatment instrument (not shown) is introduced into the body. One end side of a treatment instrument channel tube 17 is connected to the treatment instrument insertion port 16. The other end side of the treatment instrument channel tube 17 is connected to a distal end member 20 configuring a distal end portion 5 of the insertion portion 2.

The insertion portion 2 is configured by connecting the distal end portion 5, a bending portion 6, and a flexible tube portion 7 in this order from a distal end side. The distal end portion 5 is configured by mounting the distal end cover 30 for the endoscope on the distal end member 20. Details of the configuration of the distal end portion 5 will be described later.

The flexible tube portion 7 is configured to include, for example, a spiral tube, a mesh tube covering the spiral tube, and a heat-shrinkable tube configuring an outermost layer.

The bending portion 6 is configured to include a bending piece set which is configured to bend in four directions, for example, upward, downward, rightward and leftward, a mesh tube which is formed of metal and configured to cover the bending piece set, and a bending rubber serving as an envelope. The bending portion 6 is configured to be bent upward or downward by turning an up-and-down bending knob 11a of the bending operation device 11 provided to the operation portion 3 and also bent rightward or leftward by turning a right-and-left bending knob 11b.

Figure 2:
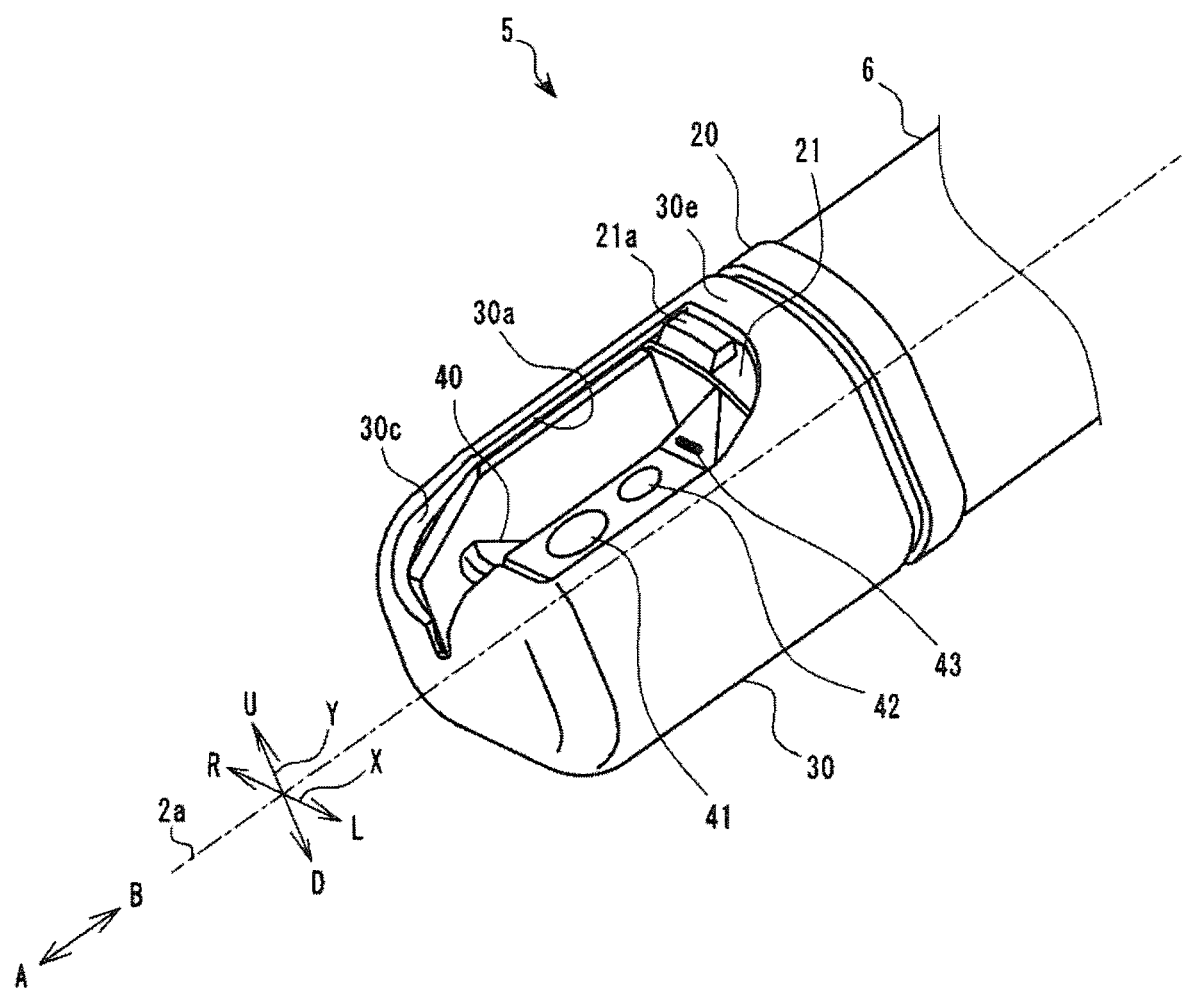
FIG. 2 is a perspective view of a distal end portion of an insertion portion.

FIG. 2 is a perspective view of the distal end portion 5. As shown in FIG. 2, the distal end portion 5 is configured by mounting the distal end cover 30 for the endoscope on the distal end member 20. The distal end cover 30 is a sheath-like member that covers a predetermined outer surface of the distal end member 20, and is attachable to and detachable from the distal end member 20. As will be described in detail later, the distal end cover 30 is provided with a break scheduled portion 35 which is a portion at which a break as an irreversible deformation occurs when the distal end cover 30 is removed from the distal end member 20 after the distal end cover 30 is once mounted on the distal end member 20.

Figure 3:
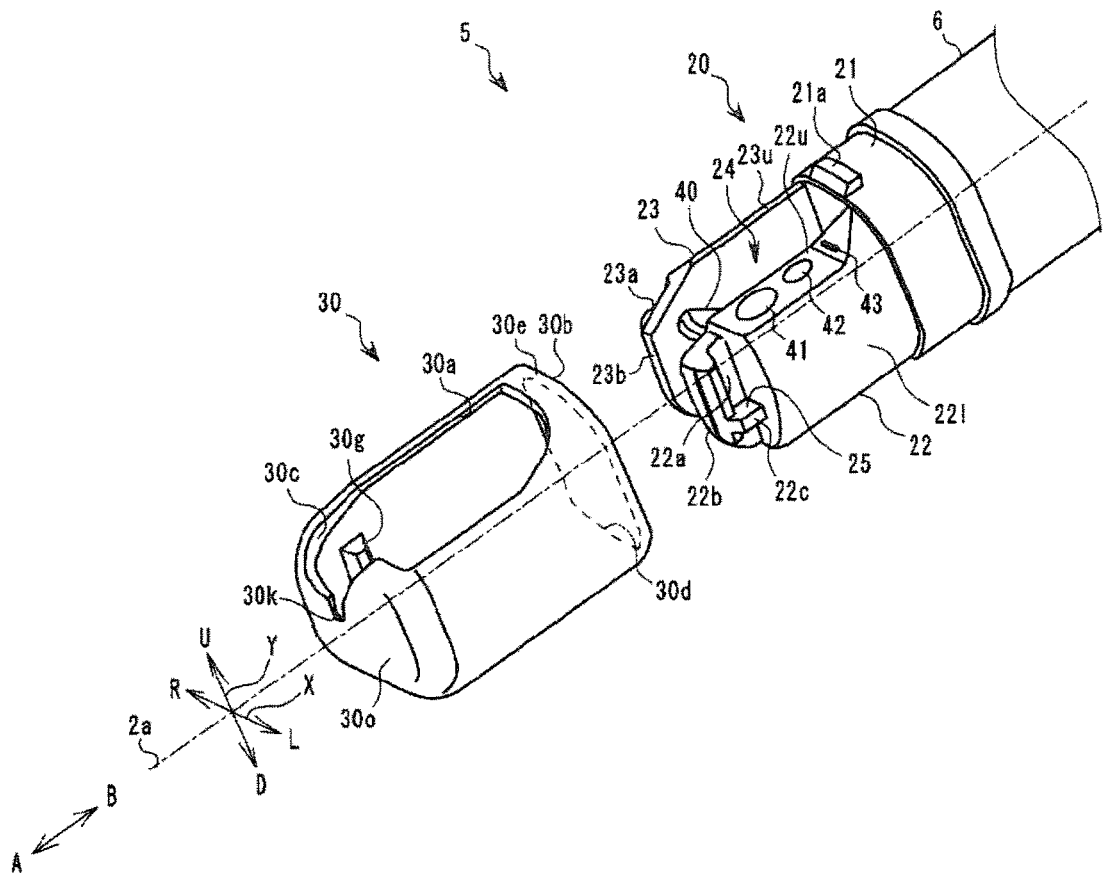
FIG. 3 is a perspective view showing a distal end cover and a distal end member in a separated state.

FIG. 3 is a perspective view showing the distal end cover 30 and the distal end member 20 in a separated state. FIG. 3 shows the distal end cover 30 in a state (unused state) where the distal end cover 30 has been never mounted on the distal end member 20.

The distal end member 20 is a rigid member configuring the distal end portion 5, and the distal end cover 30 is formed of, for example, resin having an electrical insulation property and has predetermined elasticity. A material configuring the surface of a portion of the distal end member 20 which comes into contact with the distal end cover 30 is more rigid than the resin configuring the distal end cover 30. As a result, the distal end member 20 is prevented from wearing due to repetitive replacement of the distal end cover 30.

It is preferable that the distal end cover 30 is formed of translucent or transparent resin, the color of which is the color of the raw material thereof which is not mixed with any pigment or the like. Since the distal end cover 30 is formed of translucent or transparent resin, it is easy for a user of the endoscope 1 to visually recognize whether the distal end cover 30 is correctly mounted at a predetermined position with respect to the distal end member 20. Furthermore, a contrast substance which is largely different in transmissivity of X-rays from the tissue of a subject such as a human body may be mixed in the resin constituting the distal end cover 30. This contrast substance may be mixed partially or wholly in the distal end cover 30.

Note that in the following description of the configuration of the distal end portion 5, an axis along the longitudinal direction of the elongated insertion portion 2 is referred to as an insertion portion longitudinal axis 2a. Also, a direction to the distal end side of the insertion portion 2 along the insertion portion longitudinal axis 2a is referred to as a distal end direction A, and a direction opposite to the distal end direction A is referred to as a proximal end direction B. Furthermore, two linear axes orthogonal to each other on a plane orthogonal to the insertion portion longitudinal axis 2a are defined as an X axis and a Y axis. A direction to one side along the X axis is referred to as a rightward direction R, and a direction opposite to the rightward direction R is referred to as a leftward direction L. In addition, a direction to one side along the Y axis is referred to as an upward direction U, and a direction opposite to the upward direction U is referred to as a downward direction D. The X axis and the Y axis are substantially parallel to the bending direction of the bending portion 6.

In the present embodiment, as an example, it is assumed that the right side is the rightward direction R and the upper side is the upward direction when viewing in a direction from a proximal end side to a distal end side along the insertion portion longitudinal axis 2a and setting the X axis to a horizontal direction.

Figure 4:
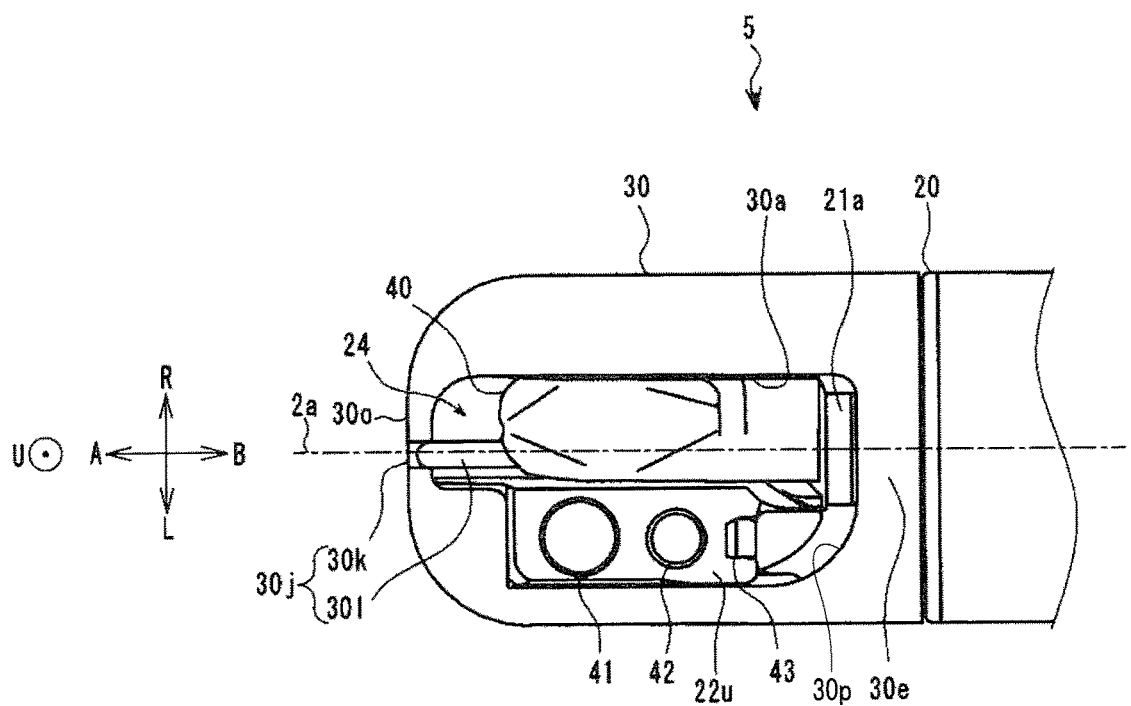
FIG. 4 is a top view of the distal end portion when the distal end portion is viewed in a direction from an upward direction side to a downward direction side.
Figure 5:
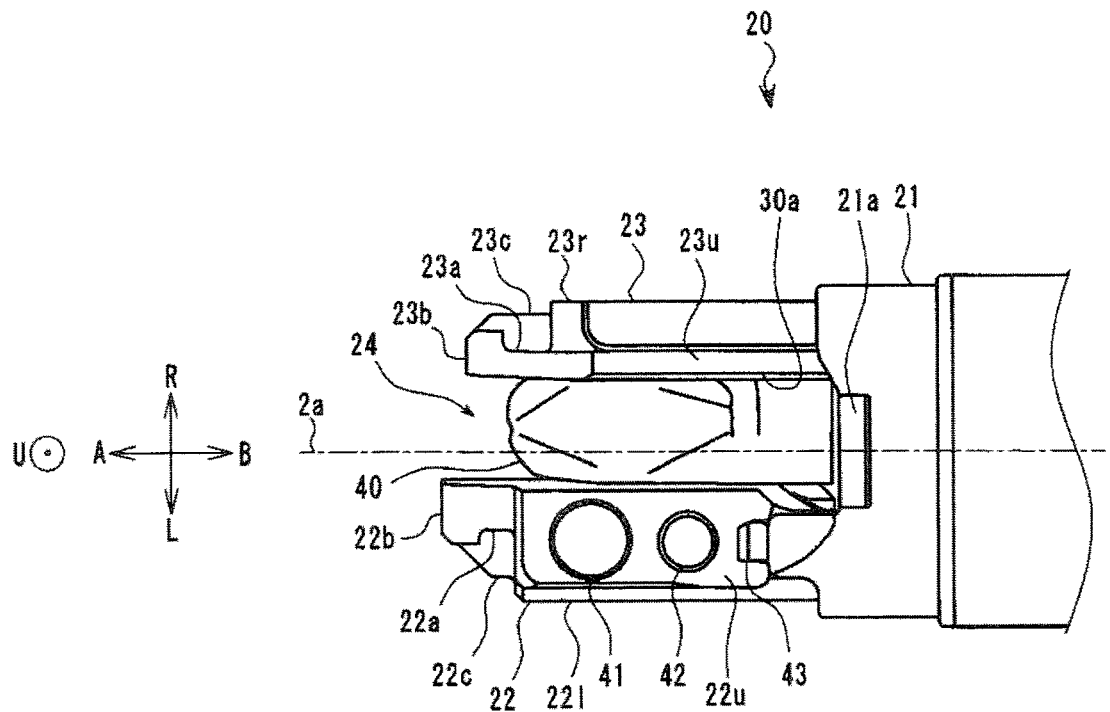
FIG. 5 is a top view of the distal end member.
Figure 6:
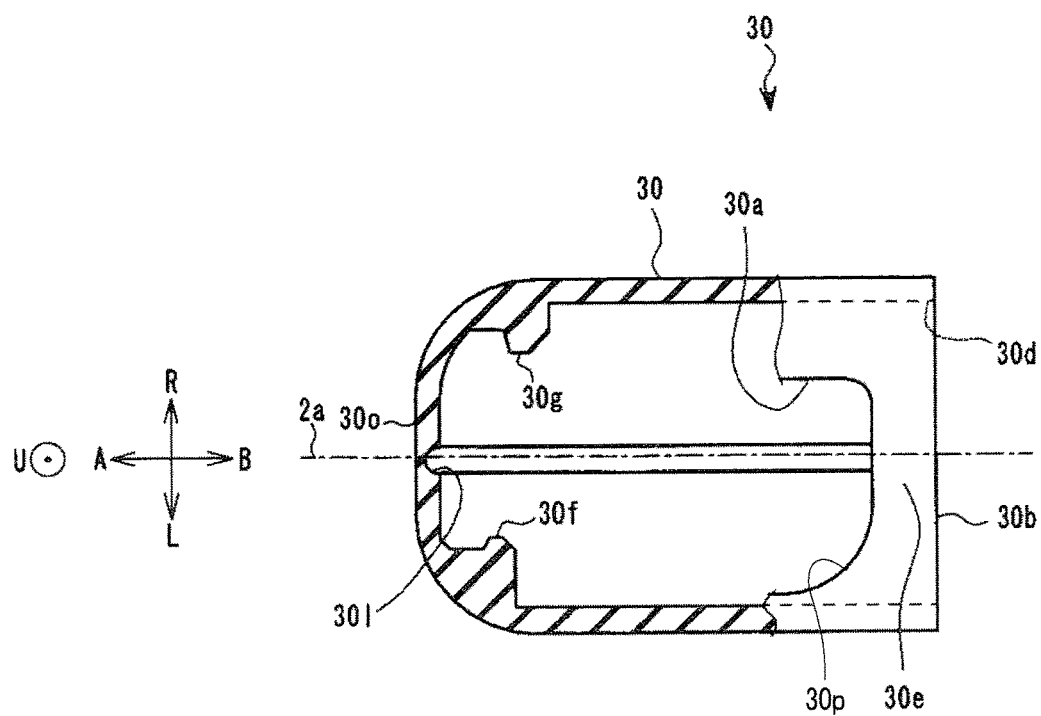
FIG. 6 is a partial cross-sectional view of the distal end cover when the distal end cover is viewed in the direction from the upward direction side to the downward direction side.

FIG. 4 is a top view of the distal end portion 5 when the distal end portion 5 is viewed in a direction from an upward direction U side to a downward direction D side. FIG. 5 is a top view of the distal end member 20. FIG. 6 is a partial cross-sectional view of the distal end cover 30 when the distal end cover 30 is viewed in the direction from the upward direction U side to the downward direction D side.

Figure 7:
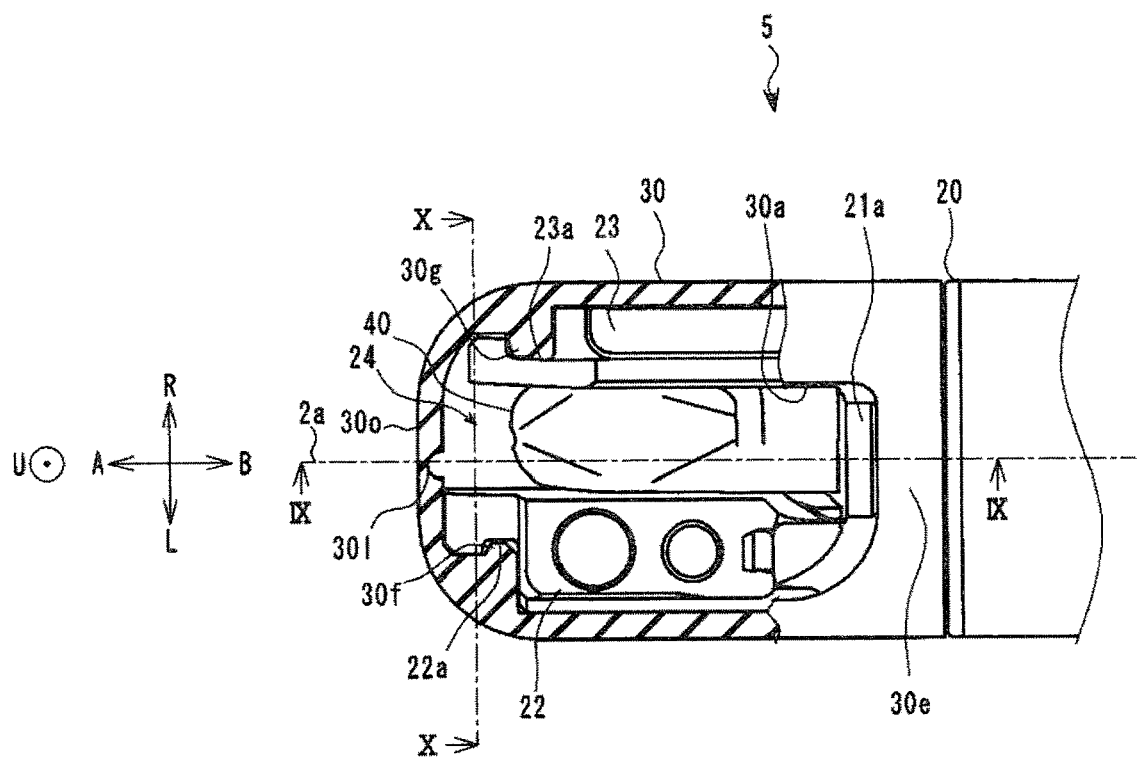
FIG. 7 is a partial cross-sectional view of the distal end portion when the distal end portion is viewed in the direction from the upward direction side to the downward direction side.
Figure 8:
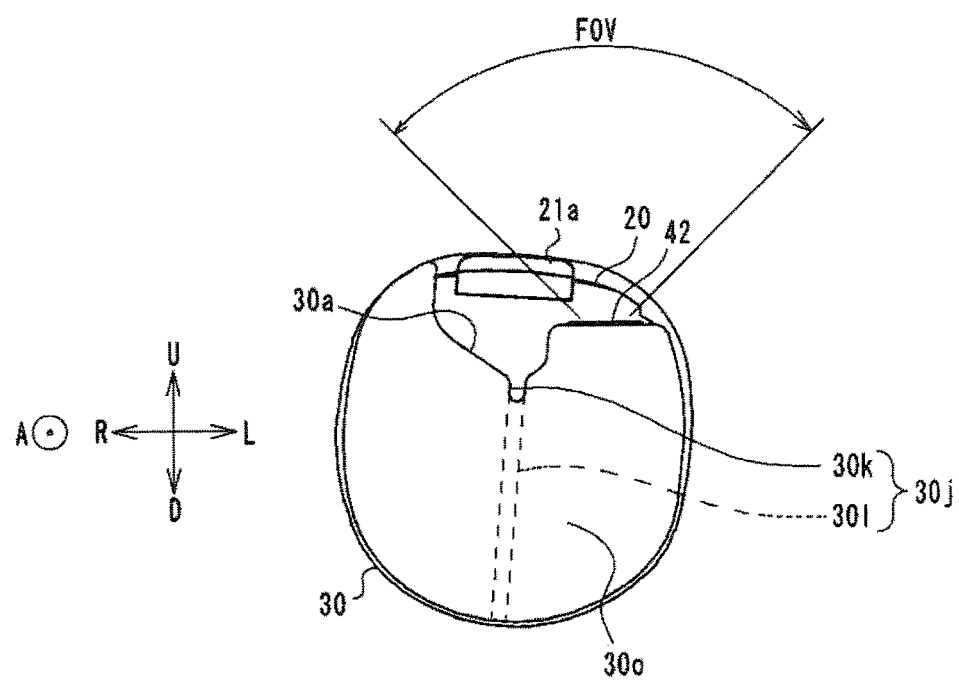
FIG. 8 is a front view of the distal end portion when the distal end portion is viewed in a direction from a distal end direction side to a proximal end direction side.
Figure 9:
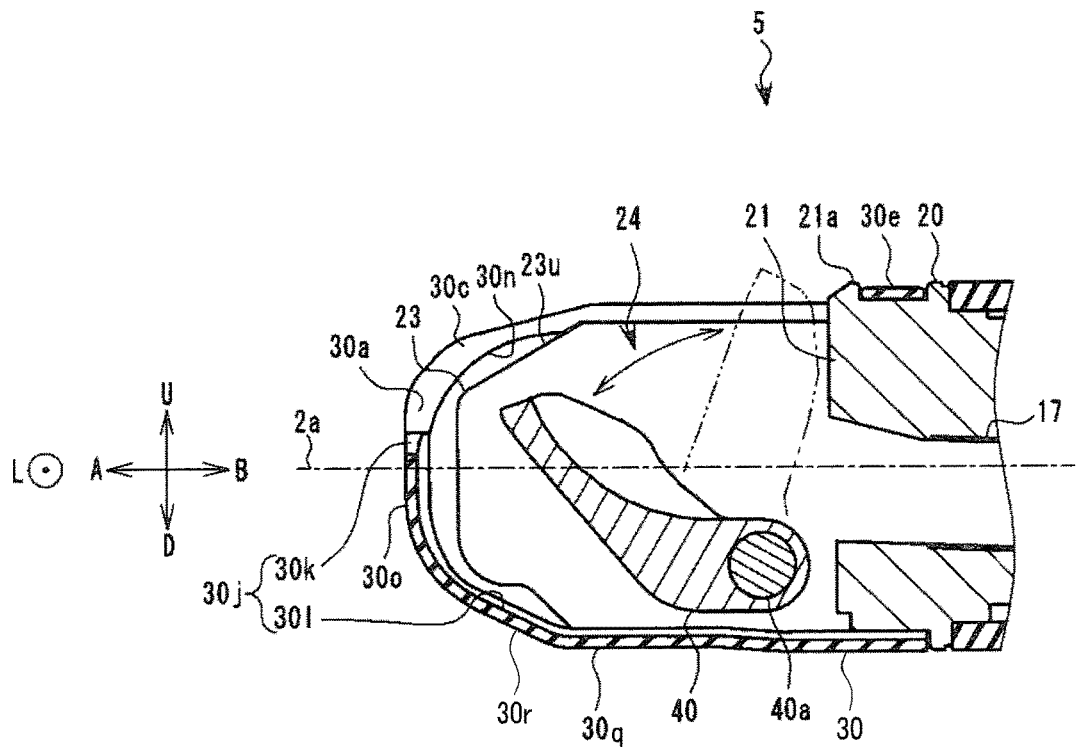
FIG. 9 is a cross-sectional view of IX-IX of FIG. 7.
Figure 10:
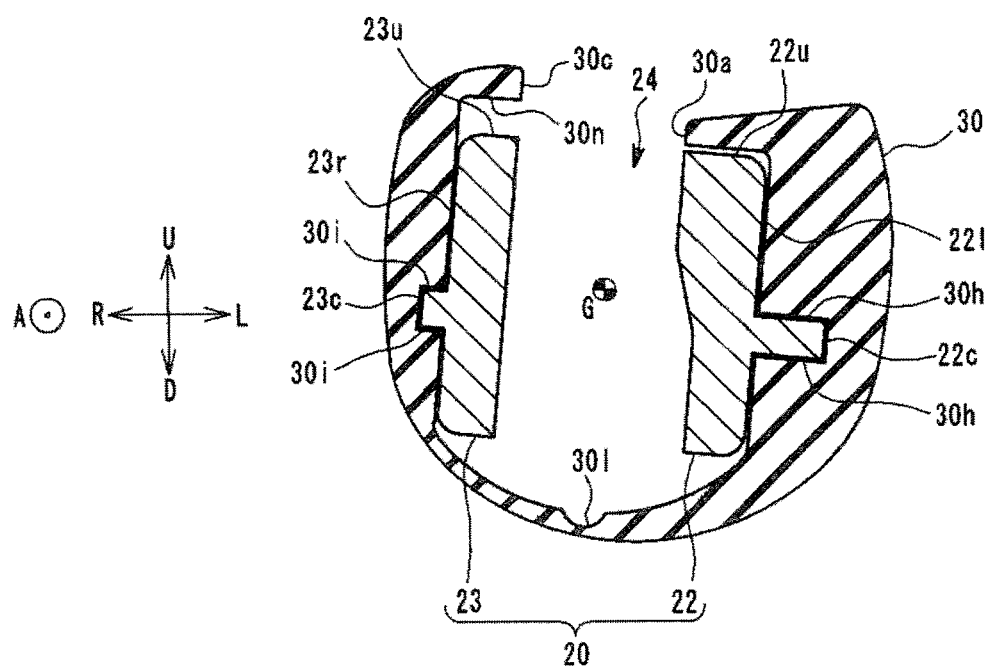
FIG. 10 is a cross-sectional view of X-X of FIG. 7.

FIG. 7 is a partial cross-sectional view of the distal end portion 5 when the distal end portion 5 is viewed in the direction from the upward direction U side to the downward direction D side. FIG. 8 is a front view of the distal end portion 5 when the distal end portion 5 is viewed in a direction from a distal end direction A side to a proximal end direction B side. FIG. 9 is a cross-sectional view of IX-IX of FIG. 7. FIG. 10 is a cross-sectional view of X-X of FIG. 7.

As shown in FIGS. 3 and 5, the distal end member 20 includes a distal end portion main body 21, a first arm portion 22 and a second arm portion 23 which are a pair of arm portions projecting from the distal end portion main body 21 along the insertion portion longitudinal axis 2a in a distal end direction A, and a raising stand accommodating space 24 which is a space formed between the first arm portion 22 and the second arm portion 23. A raising stand 40 is turnably arranged in the raising stand accommodating space 24.

The outer shape of the distal end portion main body 21 is a pillar-like shape, and a proximal end of the distal end portion main body 21 is connected to a distal end of the bending portion 6. A locking pawl 21a protruding outward is provided in an area of an outer peripheral surface of the distal end portion main body 21 which faces in an upward direction U. The locking pawl 21a is a portion to engage with an annular portion 30e of the distal end cover 30 described later.

The first arm portion 22 and the second arm portion 23 are arranged such that the raising stand accommodating space 24 which is a space formed between the first arm portion 22 and the second arm portion 23 is opened in three directions of the upward direction U, the downward direction D, and the distal end direction A. That is, the first arm portion 22 and the second arm portion 23 are arranged in a direction along the X axis with the raising stand accommodating space 24 interposed between the first arm portion 22 and the second arm portion 23. In the present embodiment, as an example, the first arm portion 22 is arranged on the leftward L side of the raising stand accommodating space 24, and the second arm portion 23 is arranged on the rightward R side of the raising stand accommodating space 24

In the present embodiment, the first arm portion 22 and the second arm portion 23 are cantilevered, and no member is provided to be bridged between the first arm portion 22 and the second arm portion 23, but a pillar-like or wall-like member configured to connect the first arm portion 22 and the second arm portion 23 may be provided between the first arm portion 22 and the second arm portion 23.

An illumination lens 41, an observation lens 42, and a cleaning nozzle 43 are arranged on an upper surface 22u of the outer peripheral surface of the first arm portion 22 which faces in the upward direction U. The observation lens 42 serves to pick up an image of a subject, and the illumination lens 41 serves to emit illumination light to the subject. As shown in FIG. 8, a field of view FOV of the observation lens 42 is centered substantially in the upward direction U. That is, the observation lens 42 puts the side of the insertion portion 2 in the field of view. The cleaning nozzle 43 is a portion configured to eject fluid to the illumination lens 41 and the observation lens 42.

As shown in FIG. 9, the raising stand 40 is arranged so as to be turnable around a pivot shaft 40a substantially parallel to the X axis in the raising stand accommodating space 24. The raising stand 40 is a tongue-like member extending in one direction from the pivot shaft 40a. FIG. 9 shows a turning range of the raising stand 40, and the raising stand 40 is turned between a first position indicated by a solid line and a second position indicated by a two-dotted chain line.

When the raising stand 40 is at the first position, the raising stand 40 is postured so as to extend substantially in the distal end direction A from the pivot shaft 40a, and wholly sandwiched between the first arm portion 22 and the second arm portion 23. When the raising stand 40 is at the second position, the raising stand 40 is postured so as to extend substantially in the upward direction U from the pivot shaft 40a, and the distal end portion is postured to protrude in the upward direction U beyond the first arm portion 22 and the second arm portion 23.

The turning operation of the raising stand 40 is performed by the raising stand operating lever 14 provided in the operation portion 3. A mechanism such as a wire configured to transmit movement of the raising stand operating lever 14 to the raising stand 40 is arranged inside the second arm portion 23.

Returning to FIGS. 3 and 5, an engaging groove 22a is engraved on a left-side surface 22l of the outer peripheral surface of the first arm portion 22, which faces in the leftward direction L. The engaging groove 22a is shaped to be concaved inward (in the rightward direction R) from the outer surface of the left-side surface 22l. Furthermore, the engaging groove 22a is provided so as to extend along the Y axis. In the present embodiment, as an example, the engaging groove 22a is arranged at a distal end portion 22b of the first arm portion 22.

An engaging groove 23a is engraved on a right-side surface 23r of the outer peripheral surface of the second arm portion 23, which faces in the rightward direction R. The engaging groove 23a is shaped to be concaved inward (in the leftward direction L) from the outer surface of the right-side surface 23r. Furthermore, the engaging groove 23a is provided so as to extend along the Y axis. In the present embodiment, as an example, the engaging groove 23a is arranged at a distal end portion 23b of the second arm portion 23.

As shown in FIG. 5, the engaging groove 22a of the first arm portion 22 and the engaging groove 23a of the second arm portion 23 are concaved portions which are opened in opposite directions along an axis substantially orthogonal to the insertion portion longitudinal axis 2a on the outer surface of the distal end member 20. The engaging grooves 22a and 23a are portions to be engaged with the locking pawls 30f and 30g of the distal end cover 30 respectively described later.

Furthermore, abutting surface portions 25 are provided on the outer peripheral surface of the distal end member 20 of the present embodiment. The abutting surface portion 25 is configured to restrict relative rotation of the distal end cover 30 around the insertion portion longitudinal axis 2a relatively to the distal end member 20 in a state where the distal end cover 30 is mounted on the distal end member 20.

In the present embodiment, the abutting surface portion 25 is a planar wall surface portion that rises up from an area of a surface extending along the insertion portion longitudinal axis 2a out of the outer peripheral surface of the distal end member 20 and is substantially parallel to the insertion portion longitudinal axis 2a.

As described in detail later, an inner peripheral surface of the distal end cover 30 is provided with rotation stopping portions 30h which are configured to abut against the abutting surface portions 25 serving as wall surface portions when there is an input for rotating the distal end cover 30 relatively to the distal end member 20, thereby resisting the input.

The shape of the abutting surface portions 25 in the present embodiment will be described more specifically. As shown in FIGS. 3 and 10, a left-side surface 22*l* of the first arm portion 22 of the distal end member 20 is provided with a plate-shaped first rib 22*c* which stands upright with respect to the left-side surface 22*l*. The first rib 22*c* is a flat plate-like portion extending along a plane parallel to the insertion portion longitudinal axis 2*a*.

Therefore, a surface of the first rib 22*c* which faces in the upward direction U and a surface of the first rib 22*c* which faces in the downward direction D are a pair of wall surface portions which rises up from the surface (the left-side surface 22*l*) extending along the insertion portion longitudinal axis 2*a* out of the outer peripheral surface of the distal end member 20 and are substantially parallel to the insertion portion longitudinal axis 2*a*. That is, the surfaces of the first rib 22*c* which face in the upward direction U and the downward direction D configure the abutting surface portions 25.

Furthermore, in the present embodiment, on a cross-section orthogonal to the insertion portion longitudinal axis 2*a*, the first rib 22*c* is arranged at a position which is biased in any one of the directions in which the abutting surface portions 25 serving as the wall surface portions face, with respect to the center-of-gravity position G derived from the contour of the distal end member 20.

Specifically, as shown in FIG. 10, the first rib 22*c* of the present embodiment is arranged at a position which is biased in the downward direction D with respect to the center-of-gravity position G derived from the contour of the distal end member 20 on a cross-section orthogonal to the insertion portion longitudinal axis 2*a*. Furthermore, the first rib 22*c* of the present embodiment is arranged at the distal end portion 22*b* of the first arm portion 22.

In the present embodiment, as an example, a plate-like second rib 23*c* which protrudes upright with respect to the right-side surface 23*r* of the second arm portion 23 of the distal end member 20 is also provided on the right-side surface 23*r*.

Next, the detailed configuration of the distal end cover 30 to be mounted on the distal end member 20 described above will be described.

As shown in FIGS. 2, 4, and 6, the distal end cover 30 is a sheath-like member which is closed on a distal end direction A side and opened on a proximal end direction B side, and covers a predetermined portion of the outer peripheral surface of the distal end member 20 while mounted on the distal end member 20.

An opening provided on the proximal end direction B side of the distal end cover 30 is referred to as an insertion port 30*d*. When the distal end cover 30 is mounted on the distal end member 20, the distal end member 20 is inserted into the distal end cover 30 via the insertion port 30*d*.

The distal end cover 30 has an opening portion 30*a* configured to expose the raising stand accommodating space 24 only in the upward direction U while mounted on the distal end member 20. Furthermore, under the state where the distal end cover 30 is mounted on the distal end member 20, the illumination lens 41, the observation lens 42, and the cleaning nozzle 43 are also exposed in the upward direction U via the opening portion 30*a*. An R portion 30*p* having a predetermined diameter is provided on an inner wall surface of the opening portion 30*a* on the proximal end direction B side of the observation lens 42.

The opening portion 30*a* is a through-hole penetrating through a part of an upper surface 30*u* facing in the upward direction U of the distal end cover 30. The opening portion 30*a* is not in contact with a proximal end 30*b* which is a proximal end in the proximal end direction B of the distal end cover 30. In other words, the opening portion 30*a* is not connected to the insertion port 30*d*. Therefore, an annular portion 30*e*, the entire periphery of which is annularly connected around the insertion portion longitudinal axis 2*a* is formed at the proximal end 30*b* of the distal end cover 30.

Under the state where the distal end cover 30 is mounted on the distal end member 20, the annular portion 30*e* is in close contact with the outer peripheral surface of the distal end portion main body 21 on the proximal end direction B side beyond the locking pawl 21*a* provided to the distal end portion main body 21. Furthermore, under this state, the locking pawl 21*a* provided to the distal end portion main body 21 protrudes into the opening portion 30*a*. That is, under the state where the distal end cover 30 is mounted on the distal end member 20, the locking pawl 21*a* engages with the annular portion 30*e*, so that the distal end cover 30 is suppressed from moving in the distal end direction A relatively to the distal end member 20. Furthermore, under this state, the locking pawl 21*a* is provided at a position where the locking pawl 21*a* is not in contact with the foregoing R portion 30*p*.

As not shown, in the present embodiment, it is preferable that an area extending along the insertion portion longitudinal axis 2*a* out of the periphery portion of the opening portion 30*a* is formed to be thick. By forming this thick wall portion at the periphery portion of the opening portion 30*a*, the opening portion 30*a* is suppressed from being deformed when the distal end member 20 is relatively pushed into the distal end cover 30 along the insertion portion longitudinal axis 2*a*, so that the locking pawl 21*a* easily passes through the inside of the annular portion 30*e*.

Furthermore, the distal end cover 30 includes locking pawls 30*f* and 30*g*, rotation stopping portions 30*h*, a finger hooking portion 30*c*, and a break inducing portion 30*j*.

As shown in FIGS. 6 and 7, the locking pawls 30*f* and 30*g* are convex portions protruding inward from the inner peripheral surface of the distal end cover 30.

The locking pawl 30*f* protrudes in the rightward direction R from an area facing in the rightward direction R of the inner peripheral surface of the distal end cover 30. The locking pawl 30*f* is arranged to engage with the engaging groove 22*a* provided on the left-side surface 22*l* of the first arm portion 22 under the state where the distal end cover 30 is mounted on the distal end member 20.

Furthermore, the locking pawl 30*g* protrudes in the leftward direction L from an area facing in the leftward direction L of the inner peripheral surface of the distal end cover 30. Under the state where the distal end cover 30 is mounted on the distal end member 20, the locking pawl 30*g* is arranged to engage with the engaging groove 23*a* provided in the right-side surface 23*r* of the second arm portion 23.

As described above, the engaging groove 22*a* of the first arm portion 22 and the engaging groove 23*a* of the second arm portion 23 are a pair of concave portions which are opened in opposite directions to each other along an axis substantially orthogonal to the insertion portion longitudinal axis 2*a* on the outer surface in the vicinity of the distal end of the distal end member 20. Accordingly, the locking pawls 30*f* and 30*g* of the distal end cover 30 engage with the engaging grooves 22*a* and 23*a*, whereby the distal end cover 30 is suppressed from moving in the distal end direction A relatively to the distal end member 20 under the state where the distal end cover 30 is mounted on the distal end member 20. By forming the distal end cover 30 of transparent or translucent resin, it can be visually recognized that the locking pawls 30f and 30g engage with the engaging grooves 22a and 23a. It is possible to visually recognize the engagement even when the whole of the distal end cover 30 is not formed of transparent or translucent resin, but only a portion where the locking pawls 30f and 30g are provided is formed of transparent or translucent resin.

As shown in FIG. 10, the rotation stopping portions 30h are provided on the inner peripheral surface of the distal end cover 30. The rotation stopping portions 30h are a configuration for restricting relative rotation of the distal end cover 30 around the insertion portion longitudinal axis 2a relatively to the distal end member 20 under the state where the distal end cover 30 is mounted on the distal end member 20.

When there is an input for rotating the distal end cover 30 around the insertion portion longitudinal axis 2a relatively to the distal end member 20 under the state where the distal end cover 30 is mounted on the distal end member 20, the rotation stopping portions 30h abut against the abutting surface portions 25 provided to the distal end member 20 to resist the input.

More specifically, the rotation stopping portions 30h are a pair of wall surface portions which are arranged so as to pinch the first rib 22c provided to the distal end member 20 from the upward direction U and the downward direction D. As described above, the abutting surface portions 25 of the present embodiment are configured to include a surface facing in the upward direction U and a surface facing in the downward direction D of the first rib 22c. The rotation stopping portions 30h of the present embodiment are configured of portions which confront the surface facing in the upward direction U and the surface facing in the downward direction D of the first rib 22c under the state where the distal end cover 30 is mounted on the distal end member 20. Note that the abutting surface portion 25 and the rotation stopping portion 30h may be in contact with each other or separated from each other under the state where the distal end cover 30 is mounted on the distal end member 20.

As described above, the first rib 22c is arranged at a position which is biased in the downward direction D with respect to the center-of-gravity center position G of the distal end member 20. Therefore, when the distal end cover 30 is attempted to be mounted on the distal end member 20 at an incorrect angle around the insertion portion longitudinal axis 2a, it is impossible to mount the distal end cover 30 because the first rib 22c is not inserted between the pair of the abutting surface portion 25.

In the present embodiment, the distal end cover 30 also has rotation stopping portions 30i including a pair of wall surface portions arranged so as to pinch the second rib 23c provided to the distal end member 20 from the upward direction U and the downward direction D. By providing the rotation stopping portions at two positions as in the case of the present embodiment, rotation of the distal end cover 30 relative to the distal end member 20 during use of the endoscope 1 can be surely suppressed. Note that in the present embodiment, as shown in FIG. 10, the positions in the upward direction U (or the downward direction D) of the first rib 22c and the second rib 23c with respect to the center-of-gravity position G are substantially equal to each other, but the positions in the upward direction U (or the downward direction D) of the first rib 22c and the second rib 23c with respect to the center-of-gravity position G may be different from each other. By changing the positions in the upward direction U (or the downward direction D) of the first rib 22c and the second rib 23c with respect to the center-of-gravity position G according to each type of products, the distal end cover 30 can be prevented from being erroneously mounted on different types of products.

As shown in FIGS. 9 and 10, the finger hooking portion 30c is provided in an area along the insertion portion longitudinal axis 2a out of the periphery portion of the opening portion 30a of the distal end cover 30, and is a portion for inputting a force for rotating the distal end cover 30 around the insertion portion longitudinal axis 2a relatively to the distal end member 20 by a finger of a person or the like under the state where the distal end cover 30 is mounted on the distal end member 20.

The area along the insertion portion longitudinal axis 2a includes two places which are an area arranged on the first arm portion 22 of the distal end member 20, and an area arranged on the second arm portion 23 under the state where the distal end cover 30 is mounted on the distal end member 20. In the present embodiment, as an example, the finger hooking portion 30c is provided in the area where the distal end cover 30 is arranged on the second arm portion 23 out of the periphery portion of the opening portion 30a.

The finger hooking portion 30c protrudes in the upward direction U beyond an upper surface 23u of the second arm portion 23 on a cross-section orthogonal to the insertion longitudinal axis 2a. Furthermore, the finger hooking portion 30c protrudes in the upward direction U beyond the area arranged on the first arm portion 22 out of the periphery portion of the opening portion 30a.

Figure 11:
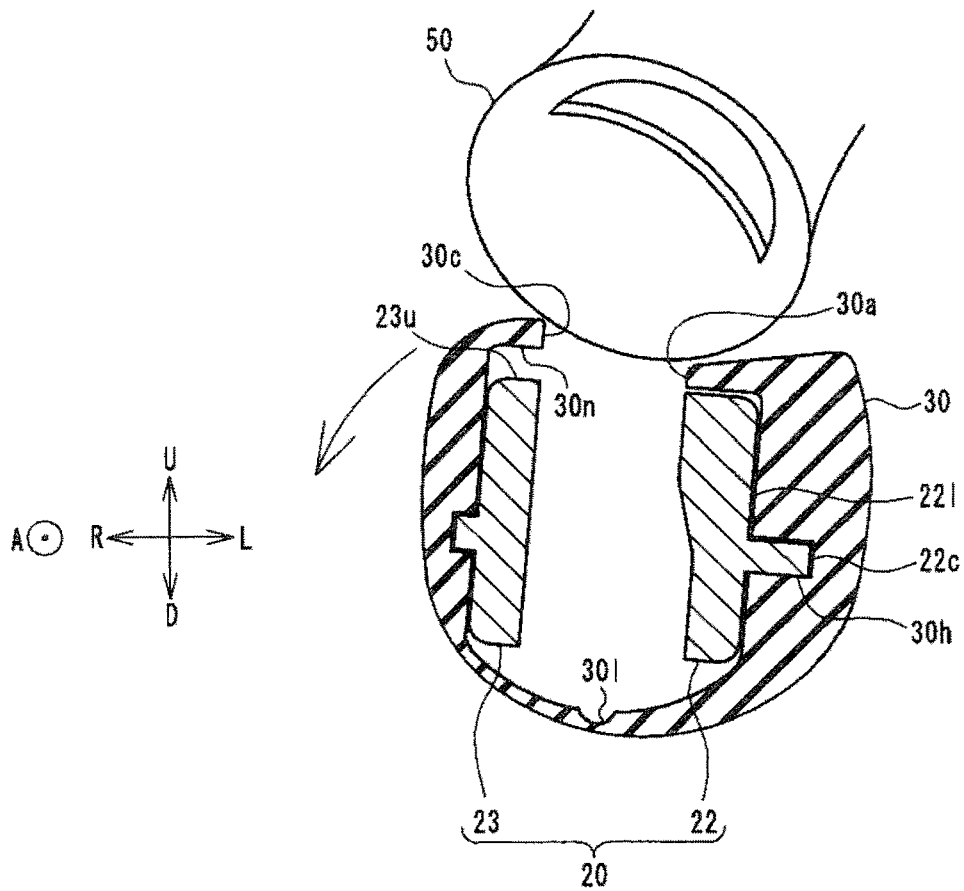
FIG. 11 is a diagram showing an aspect in which a finger is hooked on a finger hooking portion to apply force.

Since the finger hooking portion 30c protruding in the upward direction U is provided at the periphery portion of the opening portion 30a, as shown in FIG. 11, an input operation of rotating the distal end cover 30 around the insertion portion longitudinal axis 2a by a person's finger 50 is made easy. Note that the person's finger 50 is illustrated to wear no glove in FIG. 11, but in fact the fingers of a person who operates the distal end portion 5 of the endoscope 1 after use are gloved.

A gap 30n is formed between the finger hooking portion 30c and the upper surface 23u of the second arm portion 23. The gap 30n makes it easy for the person's finger 50 to input to the finger hooking portion 30c.

In the present embodiment, since the finger hooking portion 30c protruding in the upward direction U is arranged at a position where the opening portion 30a is sandwiched between the observation lens 42 and the finger hooking portion 30c, the finger hooking portion 30c is arranged at a position which is relatively far from the observation lens 42. Therefore, in the present embodiment, the finger hooking portion 30c is avoided from entering the field of view FOV of the observation lens 42 and thus narrowing an observation range of the observation lens 42. In other words, in the present embodiment, the protrusion amount of the finger hooking portion 30c in the upward direction U can be increased within a range in which the finger hooking portion 30c does not enter the field of view FOV of the observation lens 42, and input by the person's finger to the finger hooking portion 30c can be made easier.

As shown in FIG. 6, FIG. 8 and FIG. 9, the break inducing portion 30j includes a notch portion 30k and a thin wall portion 30l. The position of the notch portion 30k in an up-and-down direction (UD direction) in FIG. 8 is set so that a distal end portion of the raising stand 40 is located at a position in the downward direction D below an upper end portion in the direction U of the raising stand 40 in a state where the distal end portion of the raising stand 40 is moved in the most downward direction D.

The notch portion 30k is formed at an end portion on the distal end direction A side out of the periphery portion of the opening portion 30a. The end portion on the distal end direction A side out of the periphery portion of the opening portion 30a is located on a front surface 30o facing the distal end direction A side of the distal end cover 30.

The notch portion 30k has a shape in which the periphery portion of the opening portion 30a on the front surface 30o of the distal end cover 30 is notched in a direction substantially orthogonal to the periphery portion. In the present embodiment, the notch portion 30k is a portion obtained by notching the front surface 30o in a substantially V-shape by a predetermined length from the periphery portion of the opening portion 30a on the front surface 30o of the distal end cover 30 in the downward direction D. The shape of the notch of the notch portion 30k may be a U-shape or a rectangular shape.

The thin wall portion 30l is a linear thin wall portion extending from the front surface 30o of the distal end cover 30 to the vicinity of the proximal end 30b. Here, the thin wall portion is a portion that is smaller in thickness than the other portions of the distal end cover 30 and has weaker strength against tearing than the other portions.

The thin wall portion 30l of the present embodiment is formed by providing a groove on the inner peripheral surface of the distal end cover 30. The thin wall portion 30l extends from the notch portion 30k in the downward direction D on the front surface 30o of the distal end cover 30, and linearly extends in the proximal end direction B substantially parallel to the insertion portion longitudinal axis 2a on the side surface portion of the distal end cover 30. The thin wall portion 30l is arranged so as to pass between the pair of locking pawls 30f and 30g provided on the inner peripheral surface of the distal end cover 30.

As shown in FIG. 9, the front surface 30o and a lower surface 30q of the distal end cover 30 are connected to each other by a tapered portion 30r. Here, the lower surface 30q is a surface facing in the downward direction D on the side surface of the distal end cover 30. Furthermore, the tapered portion 30r has an outer shape that approaches to the insertion portion longitudinal axis 2a as shifting in the distal end direction A. The thin wall portion 30l is provided along the front surface 30q, the tapered portion 30r, and the lower surface 30q. The provision of the tapered portion 30r makes it easy for a break occurring at the thin wall portion 30l of the front surface 30o with the notch portion 30k as a starting point to extend in the proximal end direction B to the thin wall portion 30l of the lower surface 30q.

As shown in FIG. 9, in the present embodiment, the raising stand 40 is postured so as to extend from the pivot shaft 40a in the distal end direction A, and when the distal end portion of the raising stand 40 is moved to the most downward direction D side, the notch portion 30k is located on a downward direction D side of the distal end portion of the raising stand 40. Therefore, in the present embodiment, the treatment instrument protruding along the raising stand 40 never contacts the notch portion 30k, and thus a break is prevented from occurring in the notch portion 30k due to the contact between the notch portion 30k and the treatment instrument.

Figure 12:
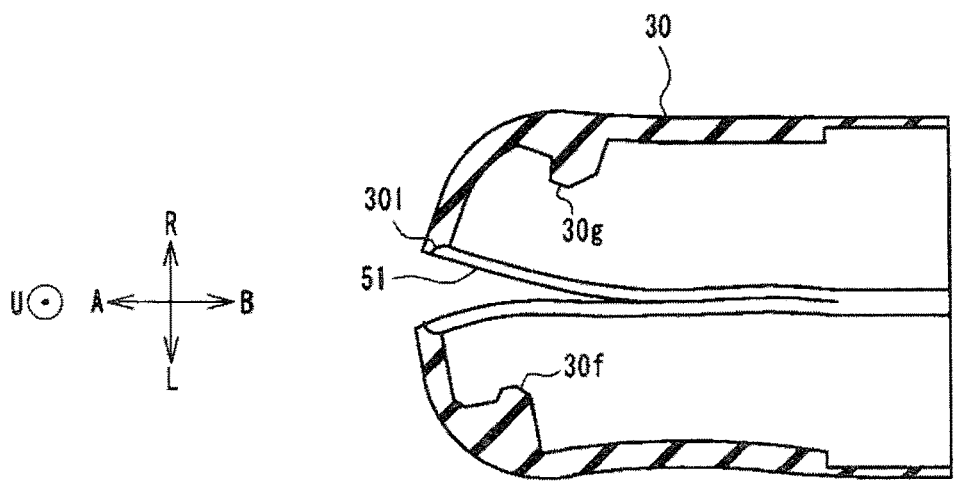
FIG. 12 is a cross-sectional view showing the distal end cover in a state where a break occurs.

Due to formation of the break inducing portion 30j, a break 51 occurs along the thin wall portion 30l with the notch portion 30k as a starting point as shown in FIG. 12 when a force acting in a direction in which the opening width of the opening portion 30a is increased in the direction of the X axis is input.

Figure 13:
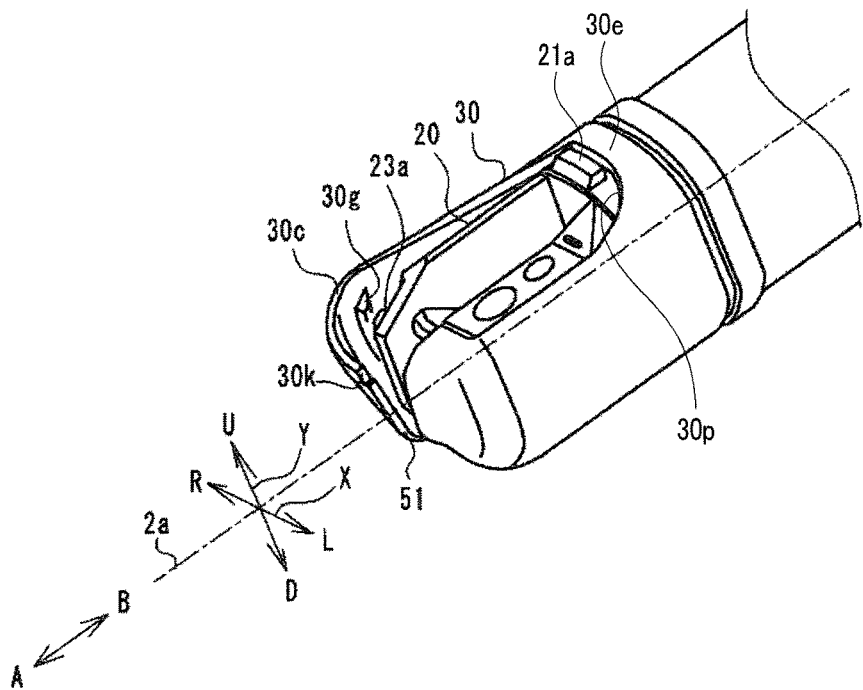
FIG. 13 is a perspective view showing the distal end member and the distal end cover in which a break has occurred.

When the break 51 occurs under the state where the distal end cover 30 is mounted on the distal end member 20, a force maintaining the distance not to widen between the pair of locking pawls 30f and 30g provided on the inner peripheral surface of the distal end cover 30. Therefore, with respect to the distal end cover 30 in which the break 51 has occurred as shown in FIG. 13, it is impossible that the locking pawls 30f and 30g are engaged with the engaging grooves 22a and 23a provided to the distal end member 20. Therefore, when the break 51 occurs under the state where the distal end cover 30 is mounted on the distal end member 20, the distal end cover 30 can be easily removed from the distal end member 20. Furthermore, it is impossible to fix the distal end cover 30 having the break 51 to the distal end member 20.

In order to make the break 51 occur in the distal end cover 30, it is necessary that a force acting in the direction in which the opening width of the opening portion 30a is increased in the X-axis direction is input to the distal end cover 30. In the present embodiment, the force acting in the direction in which the opening width of the opening portion 30a is increased in the X-axis direction can be easily input by causing a person's finger 50 to abut against the finger hooking portion 30c provided on the periphery portion of the opening portion 30a and applying a force of rotating the distal end cover 30 around the insertion portion longitudinal axis 2a as shown in FIG. 11.

Figure 14:
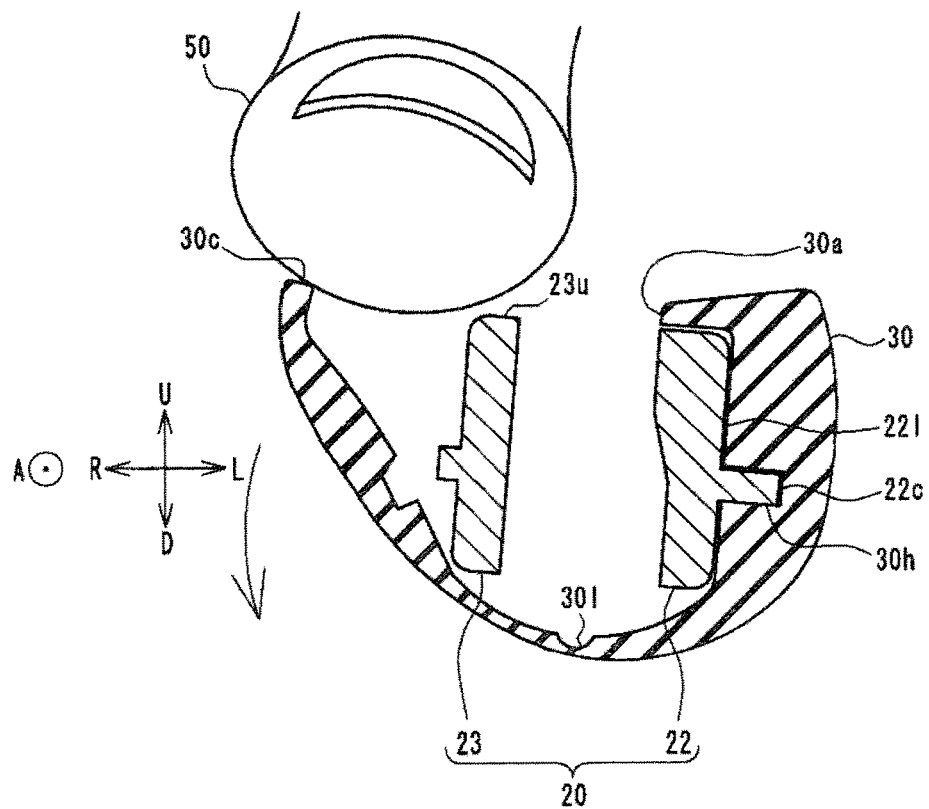
FIG. 14 is a diagram showing an aspect in which a break is caused in the distal end cover by a finger.

In the present embodiment, since the distal end cover 30 is provided with the rotation stopping portion 30h configured to restrict the rotation relative to the distal end member 20, it is unnecessary for a user to input a force of suppressing the rotation of the distal end cover 30 when a break 51 is generated in the distal end cover 30. Therefore, according to the present embodiment, the user can generate the break 51 in the distal end cover 30 by merely applying a force acting in one direction to the finger hooking portion 30c with a finger of one hand as shown in FIG. 14 while holding the distal end portion 5 with the other hand. Since the force to be applied to the distal end cover 30 acts only in one direction, the input of the force is easily performed by even a gloved finger. Furthermore, when the finger hooking portion 30c is pinched with fingers from the state shown in FIG. 14 and a force is further applied in a direction of an arrow, the distal end cover 30 itself is rotated counterclockwise in FIG. 14, the R portion 30p of the distal end cover 30 abuts against one end of the locking pawl 21a, and then the R portion 30p gets over the locking pawl 21a. At this time, the annular portion 30e is slightly increased in diameter by the locking pawl 21a. Due to the rotation of the distal end cover 14, the locking pawl 21a creeps into the inside of the annular portion 30e. Then, when the locking pawl 21a has crept inside the annular portion 30e, the distal end cover 30 can be easily removed from the distal end member 20 with a weak force by pulling the finger hooking portion 30c to the distal end direction A side.

As described above, the distal end cover 30 of the present embodiment can be easily removed from the distal end member 20 with even gloved fingers, and can be prevented from falling off the distal end member 20 during use.

In the present embodiment, on a cross-section orthogonal to the insertion portion longitudinal axis 2a, the rotation stopping portion 30h is arranged at an opposite side to the finger hooking portion 30c serving as a force input point with respect to the center-of-gravity position G derived from the contour of the distal end member 20. In other words, when the distal end cover 30 is viewed in a direction along the insertion portion longitudinal axis 2a, the finger hooking portion 30c is arranged at an opposite side to the rotation stopping portion 30h with respect to the opening portion 30a and the break inducing portion 30j. Accordingly, after an input to the finger hooking portion 30c is started by a finger 50, a portion farthest from the rotation stopping portion 30h of the cover portion 30 is first separated from the distal end member 20. Therefore, in a stage where the break 51 starts to occur in the cover portion 30, it is possible to surely maintain a state where the rotation stopping portion 30h abuts against the abutting surface portion 25.

Note that the distal end cover 30 of the present embodiment is formed of resin as described above. Here, it is assumed that the distal end cover 30 is formed by injection molding, and by making a weld line generated in the injection molding occur along the thin wall portion 30l, it is possible to further reduce the strength of the thin wall portion 30l against tearing, so that a task of removing the distal end cover 30 from the distal end member 20 is made easier.

The present invention is not limited to the above-described embodiment, and can be appropriately modified within a scope which is not contrary to the subject matter or idea of the invention readable from the claims and the whole specification, and a distal end cover for an endoscope which accompanies such a modification is also included in the technical scope of the present invention.

What is claimed is:

1. A distal end cover for an endoscope, the distal end cover being configured to be mounted on a distal end member provided with a raising stand of an insertion portion of the endoscope to cover a part of the distal end member, the distal end cover comprising:
    an opening through which a space accommodating the raising stand is exposed to an outside;
    a break inducing portion having a notch formed on a distal end side of a periphery of the opening, and a thin wall portion having a thickness smaller than a thickness of a wall adjacent to the thin wall portion, a distal end of the thin wall portion being connected to the notch, and the thin wall portion extending proximally from the notch in a proximal end direction;
    a rotation stopping surface that abuts against a wall surface protruding from an outer peripheral surface of the distal end member, thereby suppressing rotation of the distal end cover relative to the distal end member; and
    a finger hooking portion formed by protruding beyond a portion of the periphery of the opening in a radial direction in which the raising stand is raised, in a cross-section perpendicular to the insertion portion longitudinal axis, the finger hooking portion being arranged on an opposite side to the rotation stopping portion with respect to the opening and the break inducing portion when the finger hooking portion is viewed in a direction along the insertion portion longitudinal axis,
    wherein the finger hooking portion and the portion of the periphery are parts of the periphery of the opening which extend in the insertion portion longitudinal axis, and the finger hooking portion is spatially offset from the portion of the periphery in an intersecting direction intersecting the insertion portion longitudinal axis.

2. The distal end cover for endoscope according to claim 1, wherein the distal end cover is formed of transparent or translucent resin.

3. The distal end cover for the endoscope according to claim 1, wherein at least a part of the distal end cover is formed so as to have an X-ray transmittance different from an X-ray transmittance of a human body.

4. The distal end cover for endoscope according to claim 1, wherein the rotation stopping portion is arranged on a lower side of a center-of-gravity position of the distal end member when a direction in which the raising stand is raised is defined as an upward direction.

5. The distal end cover for endoscope according to claim 1, wherein a distal end surface and a lower surface of the distal end cover are connected to each other by a tapered portion.

* * * * *